United States Patent [19]
Eid et al.

[11] Patent Number: 5,167,632
[45] Date of Patent: Dec. 1, 1992

[54] SYRINGE

[75] Inventors: J. Francois Eid, Irvington, N.Y.; Edward Kearns, North Haven; James E. Kemble, Madison, both of Conn.

[73] Assignee: New Potency Products, Inc., Irvington, N.Y.

[21] Appl. No.: 825,107

[22] Filed: Jan. 24, 1992

[51] Int. Cl.$^5$ .............................................. A61M 5/20
[52] U.S. Cl. ..................................... 604/136; 604/195
[58] Field of Search ............... 604/134, 136, 137, 135, 604/195, 196, 110

[56] References Cited

U.S. PATENT DOCUMENTS

| | | |
|---|---|---|
| 2,348,337 | 5/1944 | Francis . |
| 2,696,212 | 12/1954 | Dunmire . |
| 2,769,443 | 11/1956 | Dunmire . |
| 2,940,446 | 6/1960 | Hein, Jr. . |
| 3,066,670 | 12/1962 | Stauffer . |
| 3,094,987 | 6/1963 | Dunmire . |
| 3,094,988 | 6/1963 | Dunmire . |
| 3,114,370 | 12/1963 | Kayler . |
| 3,136,313 | 6/1964 | Enstrom et al. . |
| 3,182,660 | 5/1965 | Weydanz et al. . |
| 3,334,788 | 8/1967 | Hamilton ........................ 604/135 |
| 3,543,603 | 12/1970 | Gley . |
| 3,702,609 | 11/1972 | Steiner . |
| 3,712,301 | 1/1973 | Sarnoff . |
| 3,797,489 | 3/1974 | Sarnoff . |
| 3,882,863 | 5/1975 | Sarnoff et al. . |
| 4,031,893 | 6/1977 | Kaplan et al. . |
| 4,202,314 | 5/1980 | Smirnov et al. . |
| 4,214,584 | 7/1980 | Smirnov ............................ 604/135 |
| 4,237,876 | 12/1980 | Rumph et al. . |
| 4,261,358 | 4/1981 | Vargas et al. . |
| 4,329,988 | 5/1982 | Sarnoff et al. . |
| 4,378,015 | 3/1983 | Wardlaw . |
| 4,445,510 | 5/1984 | Rigby . |
| 4,484,910 | 11/1984 | Sarnoff et al. . |
| 4,624,660 | 11/1986 | Mijers et al. . |
| 4,684,366 | 8/1987 | Denny et al. . |
| 4,723,937 | 2/1988 | Sarnoff et al. . |
| 4,787,891 | 11/1988 | Levin et al. ..................... 604/136 |
| 4,817,603 | 4/1989 | Turner et al. .................... 604/136 |
| 4,865,592 | 9/1989 | Rycroft . |
| 4,894,054 | 1/1990 | Miskinyar . |
| 4,950,265 | 8/1990 | Taylor ............................... 604/134 |
| 5,102,393 | 4/1992 | Sarnoff et al. .................... 604/136 |
| 5,114,404 | 5/1992 | Paxton et al. .................... 604/137 |

FOREIGN PATENT DOCUMENTS

| | | |
|---|---|---|
| 817939 | 8/1951 | Fed. Rep. of Germany ...... 604/136 |
| 1491696 | 5/1969 | Fed. Rep. of Germany . |
| 1538565 | 9/1968 | France . |

Primary Examiner—Paul J. Hirsch

[57] ABSTRACT

A single use automatic injection syringe having an improved locking mechanism for a coil spring that is used to provide motive force for dispensing a medicament contained therein is provided. The syringe is substantially fail-safe, inexpensive to construct and easy to operate.

10 Claims, 2 Drawing Sheets

SYRINGE

BACKGROUND OF THE INVENTION

1. Field of the Invention

This invention relates generally to disposable syringes and, in particular, to a release mechanism for a single-use, automatic injection syringe.

2. Description of the Prior Art

Disposable, one time use syringes are known and used in a variety of applications. For example, U.S. Pat. No. 3,114,370 issued to Kayler on Dec. 17, 1963 discloses a syringe designed for hypodermic injection of a liquid medicament into livestock. A barrel chamber is charged with a liquid medicament by withdrawing a plunger to its outer limit. The plunger is latched at its outer limit by a pair of latch dogs that are pivotally mounted and held in place by V-shaped spring means. The latch dogs are unseated from the plunger channel by the action of a pair of rods having sloped caming surfaces acting against the dogs.

An alternate single-use device is disclosed in U.S. Pat. No. 4,237,876 issued to Rumph et al. on Dec. 9, 1980. Rumph shows an anti-rape device designed to contain a rape-deterring fluid and to be worn within a human vagina. A ram is biased in a ready-for-use position by a detent maintained within a groove in the ram until the device is actuated.

Numerous other syringe type devices for numerous other applications are known. For example, men who have hardening of the arteries often have difficulty achieving an erection. This difficulty can be alleviated by administering an artery-dilating medication such as prostaglandin $E_1$ in the corporacavernosum of the penis to increase blood flow to the penis. The delicate nature of such a situation does, however, require a mechanism that is capable of administering the medication safely, conveniently and with a minimal risk of failure.

Accordingly, there is a need for a syringe type device with a fail-safe release mechanism for administering medication in the area of the shaft of the penis as well as in other areas.

SUMMARY OF THE INVENTION

Syringes having improved locking and release mechanisms are provided in accordance with the invention.

In one embodiment, the syringe includes a guide tube having a distal end and a proximal end. A moveable housing is slidably positioned in the guide tube and has a chamber for medicament therein. A dispensing needle is in communication with a first end of the chamber and a slidable seal assembly is positioned at the opposite end.

A piston shaft is associated with the seal assembly and includes an inner-leg holding groove in the region of the junction between the shaft and the seal assembly. A coil spring surrounds the shaft.

An outer casing is fitted over the shaft, the coil spring and the proximal end of the guide tube and is moveable with respect to the guide tube. An outer leg-holding groove is provided along an inner wall of the outer casing in alignment with the inner-leg holding groove of the piston shaft. A locking spring having a pair of inner legs and a pair of outer legs is positioned within the outer casing so that the inner legs are maintained within the inner-leg holding groove of the shaft and the outer legs are maintained within the outer-leg holding groove of the outer casing and the coil spring is maintained in a compressed condition. When the outer casing is moved in the direction of the distal end of the guide tube, both the inner and the outer legs of the locking spring disengage and the coil spring is allowed to expand. This permits the dispensing needle to pass through the distal end of the guide tube and dispense the medicament contained in the chamber.

In another embodiment, the syringe includes a trigger tube that has a distal end, a locking end with an opening therethrough opposite the distal end, and a side wall between the distal end and the locking end that adjoins the locking end at a perimeter edge with a detent portion and a non-detent portion.

A moveable housing with a medicament chamber therein is slidably positioned in the trigger tube, a dispensing needle is in communication with the chamber at a first end and a seal assembly is slidably positioned in the chamber at a second end that is opposite the first end.

A piston shaft is associated with the seal assembly at a first end of the shaft (the "seal assembly" portion of the shaft) and has a groove at an opposing end (the "locking member" portion of the shaft). The locking member portion extends through the opening in the trigger tube and a coil spring surrounds the shaft within the tube.

A locking lever with an opening therethrough fits over the trigger tube and the locking member portion of the shaft also extends through the opening in the locking lever. The locking lever has a flange extending in the direction of the distal end of the trigger tube so that the opening in the locking lever is offset from the opening in the trigger tube and the locking member portion of the shaft cannot slide through the opening in the locking lever when the flange is adjacent the non-detent portion of the perimeter edge. When the flange is rotated to the detent portion and pushed into that portion, the shaft is released and the coil spring expands to cause movement of the housing and release of the medicament.

Accordingly, it is an object of the invention to provide an improved syringe having a substantially fail-safe release mechanism.

Another object of the invention is to provide an improved syringe with a spring-loaded release mechanism.

A further object of the invention is to provide an improved syringe that is easy to use.

Still another object of the invention is to provide an improved single use, automatic injection syringe.

Still another object of the invention is to provide an improved syringe that can be disposed of safely.

Yet another object of the invention is to provide an improved syringe that is inexpensive to manufacture.

Further objects and advantages of the invention will be apparent from the specification. The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the invention, reference is made to the following description taken in connection with the accompanying drawings, in which.

DESCRIPTION OF THE PREFERRED EMBODIMENTS

Figure 1:
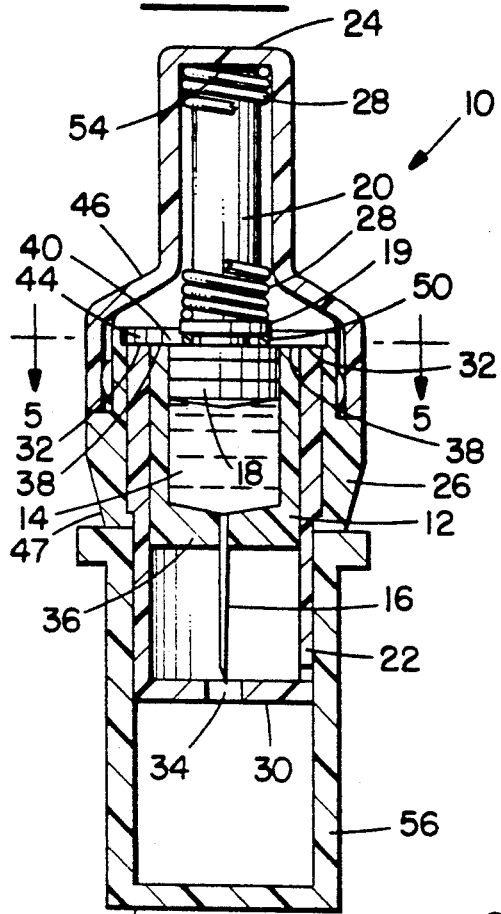
FIG. 1 is a cross sectional view of a circular syringe constructed and arranged in accordance with the invention shown in an as-sold condition.
Figure 2:
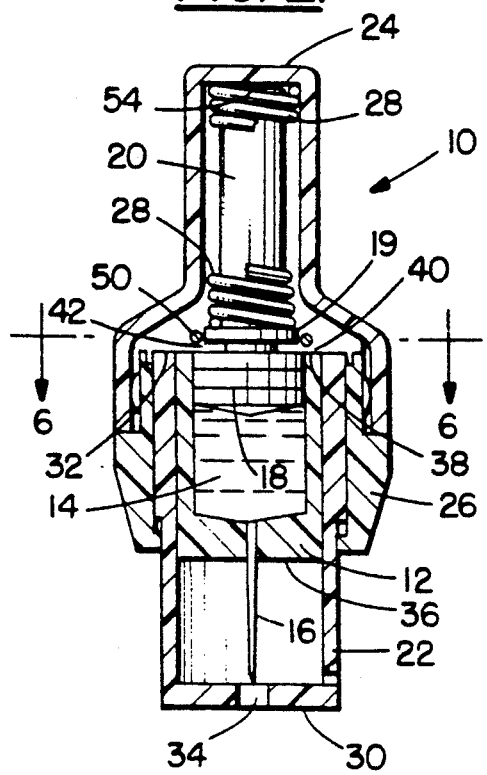
FIG. 2 is a cross sectional view of the syringe shown in a ready-for-use condition.
Figure 3:
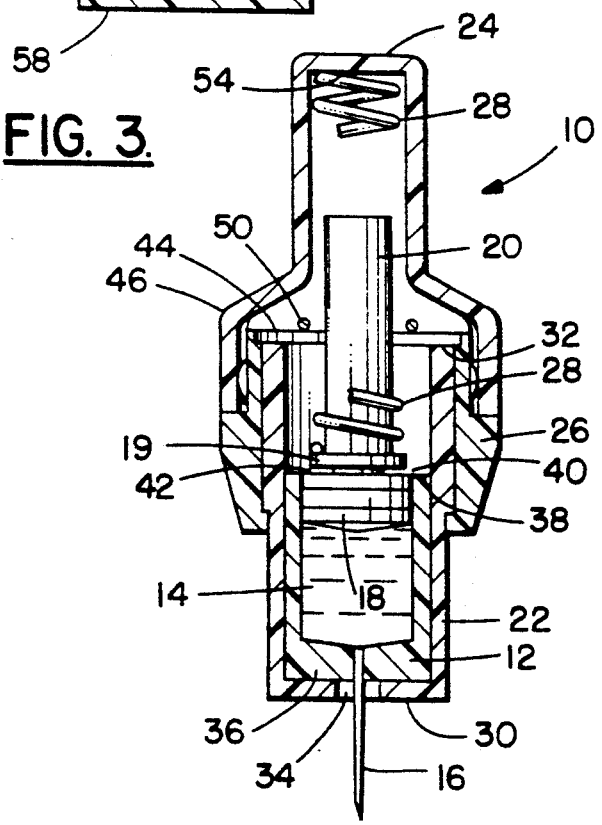
FIG. 3 is a cross sectional view of the syringe shown in an in-use condition.
Figure 4:
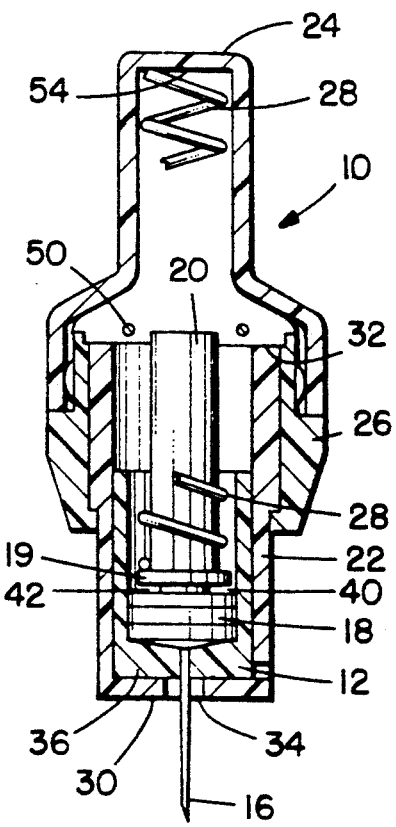
FIG. 4 is a cross sectional view of the syringe shown in an after-use condition.
Figure 5:
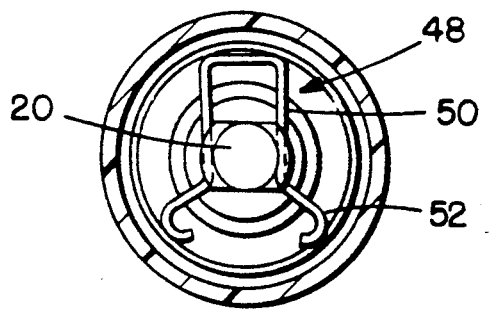
FIG. 5 is a cross sectional view of the syringe taken through section line 5—5 of FIG. 1.
Figure 6:
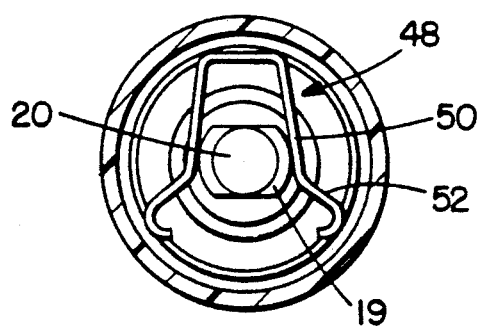
FIG. 6 is a cross sectional view of the syringe taken through section line 6—6 of FIG. 2.

Reference is made to FIGS. 1-6 wherein a syringe 10 constructed and arranged in accordance with a first embodiment of the invention is depicted. The syringe 10 is of a generally circular form, as shown specifically in the cross sections of FIGS. 5 and 6.

The syringe 10 includes a guide tube 22 for guiding a moveable housing 12. The guide tube 22 includes a distal end 30 and a proximal, open end 32. The distal end 30 of the guide tube 22 is constructed of a material that is of sufficient strength to maintain the movable housing 12 therein even when force is applied. The distal end 30 includes an aperture 34 for the passage of needle 16. If desired, aperture 34 can be filled with a material such as rubber, that can readily be punctured by a needle.

The moveable housing 12 fits within the guide tube 22 and is slidable therein. The moveable housing 12 includes a chamber 14 that is adapted to contain a medicament. The medicament is any suitable liquid medicament that can be dispensed through a needle. In a preferred embodiment, the medicament is one capable of being maintained under ambient conditions for an extended period since the syringes of the invention are intended to be marketed in a pre-filled condition for one time use.

A dispensing needle 16 is provided at a first end 36 of the moveable housing 12 in communication with the medicament chamber 14. The dispensing needle 16 is initially seated so as to abut aperture 34 of the distal end 30 of the guide tube 22.

A seal assembly 18 is initially positioned at a second end 38 of the moveable housing 12 opposite the first end 36. The seal assembly 18 is slidable within the moveable housing 12 when sufficient force is applied. Prior to application of sufficient force, the seal assembly 18 maintains medicament without spillage or leakage in the medicament chamber 14 of the moveable housing 12.

A piston shaft 20 is affixed to the seal assembly 18 on its outer side 40 opposite the medicament chamber 14. The configuration of the piston shaft 20 is such that an inner leg holding groove 42 is formed between the outer side 40 of the seal assembly 18 and a shoulder 19 formed on the outside surface of the piston shaft 20.

A coil spring 28 surrounds the piston shaft 20 and an outer casing or housing 26 covers the shaft 20, the coil spring 28 and the open end 32 of the guide tube 22.

Housing 26 is composed of two separable portions 46 and 47 to allow assembly of the syringe. The outer casing or housing 26 is moveable with respect to the guide tube 22 and further includes an outer leg holding groove or shoulder 44 along an inner wall of portion 47 adjacent to the position where the piston shaft 20 is affixed to the seal assembly 18 to form the inner leg holding groove 42.

A locking spring 48 having a pair of inner legs 50 and a pair of outer legs 52 is initially positioned within the outer casing 26 so that the inner legs 50 are positioned within the inner leg holding groove 42 of the shaft 20 and the outer legs are maintained within the outer leg holding groove 44 of the housing 26. This configuration serves to maintain the coil spring 28 in a compressed condition between shoulder 19 on piston shaft 20 and the opposite inner wall portion 54 of the outer casing 26.

Figure 7:
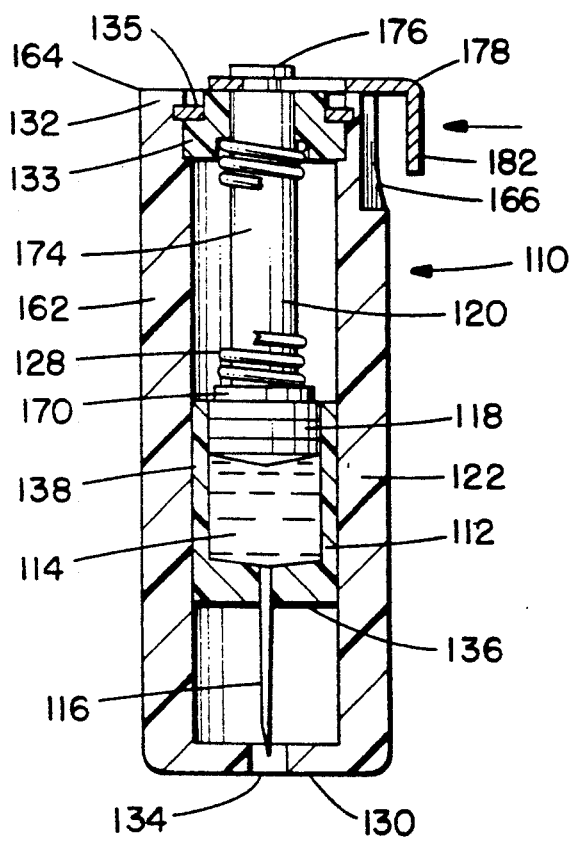
FIG. 7 is a cross sectional view of a circular syringe constructed and arranged in accordance with an alternate embodiment of the invention shown in a ready-for-use condition.
Figure 8:
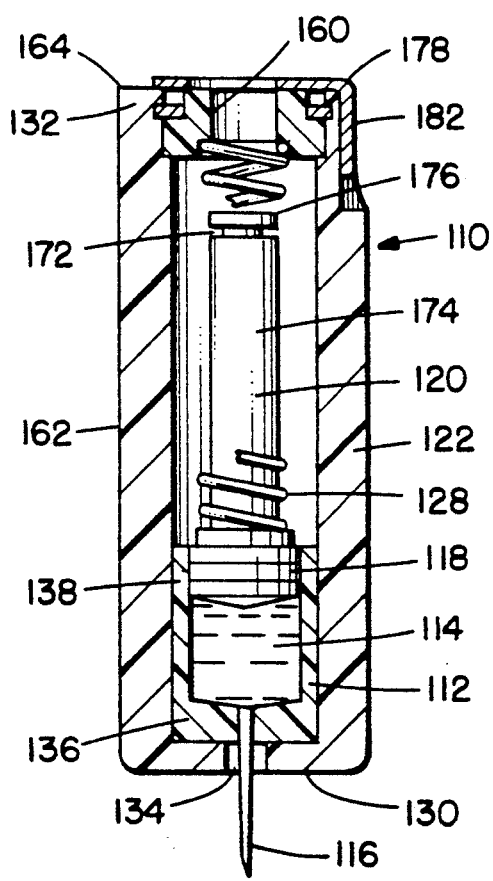
FIG. 8 is a cross sectional view of the alternate embodiment in an in-use condition.
Figure 9:
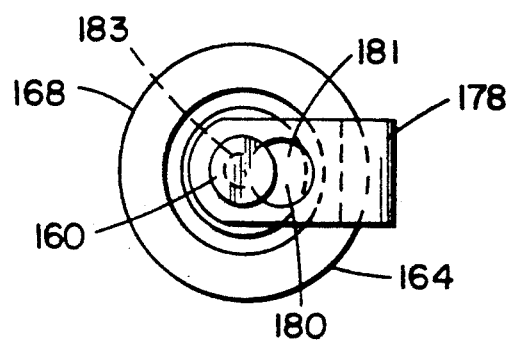
FIG. 9 is a top view of the alternate embodiment in the ready-for-use condition.
Figure 10:
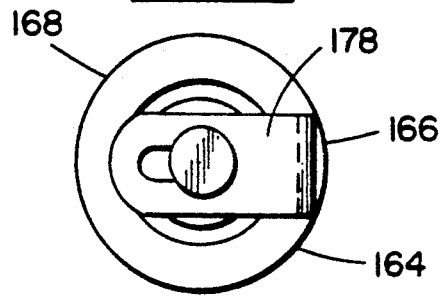
FIG. 10 is a top view of the alternate embodiment in the in-use condition.

A removable protective cap 56 is provided and fits over the guide tube 22 to protect the distal end 30. The distance between the distal end 30 of the guide tube 22 and the opposing closed end 58 of the cap 56 is approximately the length of the dispensing needle 16. Although not shown in the figures, a similar protective cap can be used with the alternate embodiment of FIGS. 7-10.

To use the syringe 10, the protective cap 56 is removed from the distal end 30 of the guide tube 22 and the syringe 10 is positioned at a desired location for injection of the medicament contained in the medicament chamber 14. Force is applied to the plunger end 24 of the outer casing or housing 26 to force the housing 26 towards the distal end 30 of the guide tube 22. This simultaneously causes the piston shaft 20 and the seal assembly 18 of the moveable housing 12 to move out of engagement with the locking spring 48. Specifically, the outer legs 52 of the locking spring 48 move out of engagement with the outer leg holding groove 44 in the outer casing or housing 26 and the inner legs 50 move out of engagement with the inner leg holding groove 42 of the shaft 20. Consequently, the coil spring 28 is freed from its compressed condition and begins to expand.

Initially, there is greater friction between the seal assembly 18 and the moveable housing 12 than there is between the moveable housing 12 and the guide tube 22. Therefore, the entire moveable housing 12 moves within the guide tube 22 towards the distal end 30 and the dispensing needle 16 passes through aperture 34 of the distal end 30.

When the moveable housing 12 abuts the distal end 30 of the guide tube 22, the coil spring is in a partially, but not fully, expanded condition. Consequently, the seal assembly 18 begins to move within the medicament chamber 14 of the moveable housing 12 and forces the medicament contained therein through the dispensing needle 16. The protective cap 56 is replaced on the guide tube 22 to cover the dispensing needle 16 and prevent needle sticks or stabs after use.

The needle 16 used with the syringe will depend on the application. For example, in the case of a syringe used to administer an artery-dilating medication to a patient's penis, a needle having an outside diameter of 29 or 30 gauge is used to prevent long term damage to the penile shaft from repeated injections. The inside diameter of the needle is selected based on the viscosity of the medication so as to achieve a dispensing time of, for example, approximately ten seconds.

An alternate embodiment of the invention is depicted in FIGS. 7-10. A syringe 110 includes trigger tube 122 having a distal end 130 and a proximal, locking end 132.

The distal end 130 includes an aperture 134 which can be sealed with a needle-puncturable material. The locking end 132 includes a plug 133 which is received into the mouth of trigger tube 122 and held in place by snap ring 135. Plug 133 includes an opening 160.

A side wall 162 adjoins the distal end 130 and the locking end 132. A perimeter edge 164 is formed where the side wall 162 adjoins the locking end 132. The perimeter edge 164 includes a detent portion 166 and a non-detent portion 168.

A moveable housing 112 is positioned in the trigger tube 122 and includes a medicament chamber 114. A dispensing needle 116 is in communication with the chamber 114 at a first end 136 of the housing 112.

A seal assembly 118 is slidably positioned at a second end 138 of the moveable housing 112 nearest the locking end 132 of the trigger tube 122 and opposite the first end 136 of the housing 112.

A shaft 120 is affixed to the seal assembly 118 at a first end 170 of the shaft 120. A groove 172 is formed in the shaft 120 and divides the shaft 120 into a seal assembly affixed portion 174 and a locking member portion 176. A coil spring 128 surrounds the shaft 120 within the trigger tube 122.

Initially, the shaft 120 is positioned so that the locking member portion 176 extends through the opening 160 in plug 133. A locking lever 178 having an opening 180 therethrough is positioned outside the trigger tube 122 at the locking end 132 and the locking member portion 176 of the shaft 120 extends through the opening 180. Opening 180 includes a first portion 181 through which locking member portion 176 of shaft 120 can pass and a second portion 183 through which portion 176 cannot pass. Initially, portion 183 of opening 180 is in engagement with groove 172 of shaft 120 so as to maintain the coil spring 128 in an initially compressed condition between the first end 170 of the shaft 120 and plug 133.

A flange 182 on the locking lever 178 extends over the perimeter edge 164 of the trigger tube 122 in the direction of the distal end 130. The opening 180 in the locking lever 178 is offset from the opening 160 in plug 133 when the flange 182 extends over the non-detent portion 168 of the perimeter edge 164. Similarly, portion 183 of opening 180 is in engagement with groove 172 of shaft 120 when flange 182 extends over the non-detent portion 168 of the perimeter edge 164.

To use the syringe 110 provided in accordance with this embodiment of the invention, the flange 182 of the locking lever 178 is rotated to align with the detent portion 166 of the perimeter edge 164 of the trigger tube 122. The flange is then pushed into the detent. This causes portion 181 of the opening 180 in the locking lever 178 to align with the opening 160 in plug 133. Accordingly, the locking member portion 176 of the shaft 120 slides through the openings 180 and 160 and permits expansion of the coil spring 128. In turn, expansion of the coil spring 128 causes the moveable housing 112 to move toward the distal end 130 of the trigger tube 122, the dispensing needle 116 to pass through aperture 134 of the trigger tube 122 and medicament to be dispensed from the medicament chamber 114 as seal assembly 118 moves within the chamber. As with the first embodiment, the frictional levels between seal assembly 118 and moveable housing 112, and between moveable housing 112 and trigger tube 122 are chosen so that the housing moves in the tube before the seal assembly moves in the housing.

The disposable syringes of the present invention can be made of a variety of materials known to persons skilled in the art. For example, the various housings and casings can be made of a sterilizable plastic such as polyethylene or polypropylene. Similarly, the seal assembly can be made of a sterilizable elastomer such as silicone rubber, and the springs, levers, and the like can be made of, for example, stainless steel.

It will thus be seen that the objects set forth above, among those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

It is also to be understood that the following claims cover all of the generic and specific features of the invention herein described and all statements of the scope of the invention which, as a matter of language, might be said to fall therebetween.

What is claimed is:

1. A syringe comprising:
   a guide tube having a distal end and a proximal end;
   a moveable housing positioned in the guide tube and having a chamber adapted to contain a medicament therein;
   a dispensing needle in communication with the chamber at a first end thereof for dispensing medicament therethrough;
   a seal assembly slidably positioned within the chamber for movement towards the first end;
   a shaft associated with the seal assembly and including an inner-leg holding groove;
   a coil spring surrounding the shaft;
   an outer casing covering the shaft, the coil spring and the proximal end of the guide tube so as to be moveable with respect to the guide tube and having an outer-leg holding groove along an inner wall thereof;
   a locking spring having a pair of inner legs and a pair of outer legs and initially positioned within the outer casing so that the inner legs are maintained within the inner-leg holding groove of the shaft and the outer legs are maintained within the outer-leg holding groove of the outer casing so as to maintain the coil spring in a compressed condition;
   wherein movement of the outer casing towards the distal end of the guide tube causes the outer legs of the locking spring to disengage from the outer-leg holding groove in the outer casing and the inner legs to disengage from the inner-leg holding groove of the shaft so as to release the coil spring from its compressed condition.

2. The syringe of claim 1 wherein the release of the coil spring from its compressed condition initially causes the moveable housing to move within the guide tube without substantial movement of the seal assembly within the chamber.

3. The syringe of claim 1 further comprising a removable cap adapted to be positioned over the distal end of the guide tube.

4. The syringe of claim 1 further comprising a liquid medicament in the medicament chamber.

5. The syringe of claim 4 wherein the medicament is an artery-dilating medication.

6. A syringe comprising:

a trigger tube having a distal end, a proximal end, and a side wall between the distal and proximal ends, said side wall in the region of the proximal end including a detent portion and a non-detent portion;

a moveable housing positioned in the trigger tube and having a chamber adapted to contain a medicament therein;

a dispensing needle in communication with the chamber at a first end thereof for dispensing medicament therethrough:

a seal assembly slidably positioned within the chamber for movement towards the first end;

a shaft having a proximal end and a distal end, the distal end being associated with the seal assembly and the proximal end including a groove;

a coil spring surrounding the shaft;

a locking lever positioned outside the trigger tube and having (a) an opening therethrough which includes a first portion for engaging the groove and a second portion through which the proximal end of the shaft can pass and (b) a flange extending along the side wall of the trigger tube in the direction of the trigger tube's distal end, said locking lever being rotatable about the shaft when the first portion of the opening and the groove are in engagement, wherein the shaft is prevented from moving distally when the first portion of the opening is in engagement with the groove and the shaft is released and allowed to move distally when the locking lever is rotated about the shaft until the flange is aligned with the detent portion of the side wall and pushed into the detent portion so as to move the first portion of the opening out of engagement with the groove and bring the second portion of the opening into alignment with the proximal end of the shaft 7. The syringe of claim 6 wherein the release of the shaft initially causes the moveable housing to move within the trigger tube without substantial movement of the seal assembly within the chamber.

8. The syringe of claim 6 further comprising a removable cap adapted to be positioned over the distal end of the trigger tube.

9. The syringe of claim 6 further comprising a liquid medicament in the medicament chamber.

10. The syringe of claim 9 wherein the medicament is an artery-dilating medication.

* * * * *